United States Patent [19]
Watts

[11] Patent Number: 5,120,309
[45] Date of Patent: Jun. 9, 1992

[54] HYPODERMIC SYRINGE WITH PROTECTIVE SHIELD

[76] Inventor: Kenneth A. Watts, 20816 N. 20th Ave., Unit 1, Phoenix, Ariz. 85027

[21] Appl. No.: 364,253

[22] Filed: Jun. 9, 1989

[51] Int. Cl.⁵ .............................................. A61M 5/00
[52] U.S. Cl. ................................. 604/110; 604/198; 604/263
[58] Field of Search ............... 604/197, 198, 192, 194, 604/162, 263, 110, 280, 264; 128/763, 770

[56] References Cited

U.S. PATENT DOCUMENTS

| | | | |
|---|---|---|---|
| 2,571,653 | 10/1951 | Bastien | 604/198 |
| 4,425,120 | 1/1984 | Sampson et al. | 604/263 |
| 4,738,663 | 4/1988 | Bogan | 604/198 |
| 4,826,490 | 5/1989 | Byrne et al. | 604/110 |
| 4,840,185 | 6/1989 | Hernandez | 604/198 |
| 4,840,619 | 6/1989 | Hughes | 604/198 |
| 4,846,796 | 7/1989 | Carrell et al. | 604/198 |
| 4,850,374 | 7/1989 | Diaz-Ramos | 604/198 |
| 4,874,383 | 10/1989 | McNaughton | 604/198 |
| 4,892,107 | 1/1990 | Haber | 604/198 |
| 4,900,310 | 2/1990 | Ogle, II | 604/263 |
| 4,923,447 | 5/1990 | Morgan | 604/198 |
| 4,946,441 | 8/1990 | Laderoute | 604/110 |

Primary Examiner—C. Fred Rosenbaum
Assistant Examiner—Kathleen A. Doley
Attorney, Agent, or Firm—Allen A. Dicke, Jr.

[57] ABSTRACT

The protective shield for a hypodermic syringe includes a tubular body which overlies the needle of the syringe when the shield is in the forward position. The protective shield has an opening therein to permit exposure of the needle when the shield is in the retracted position. A detent engages the syringe and the shield to limit relative motion therebetween and to releasably lock the shield in its end positions.

19 Claims, 2 Drawing Sheets

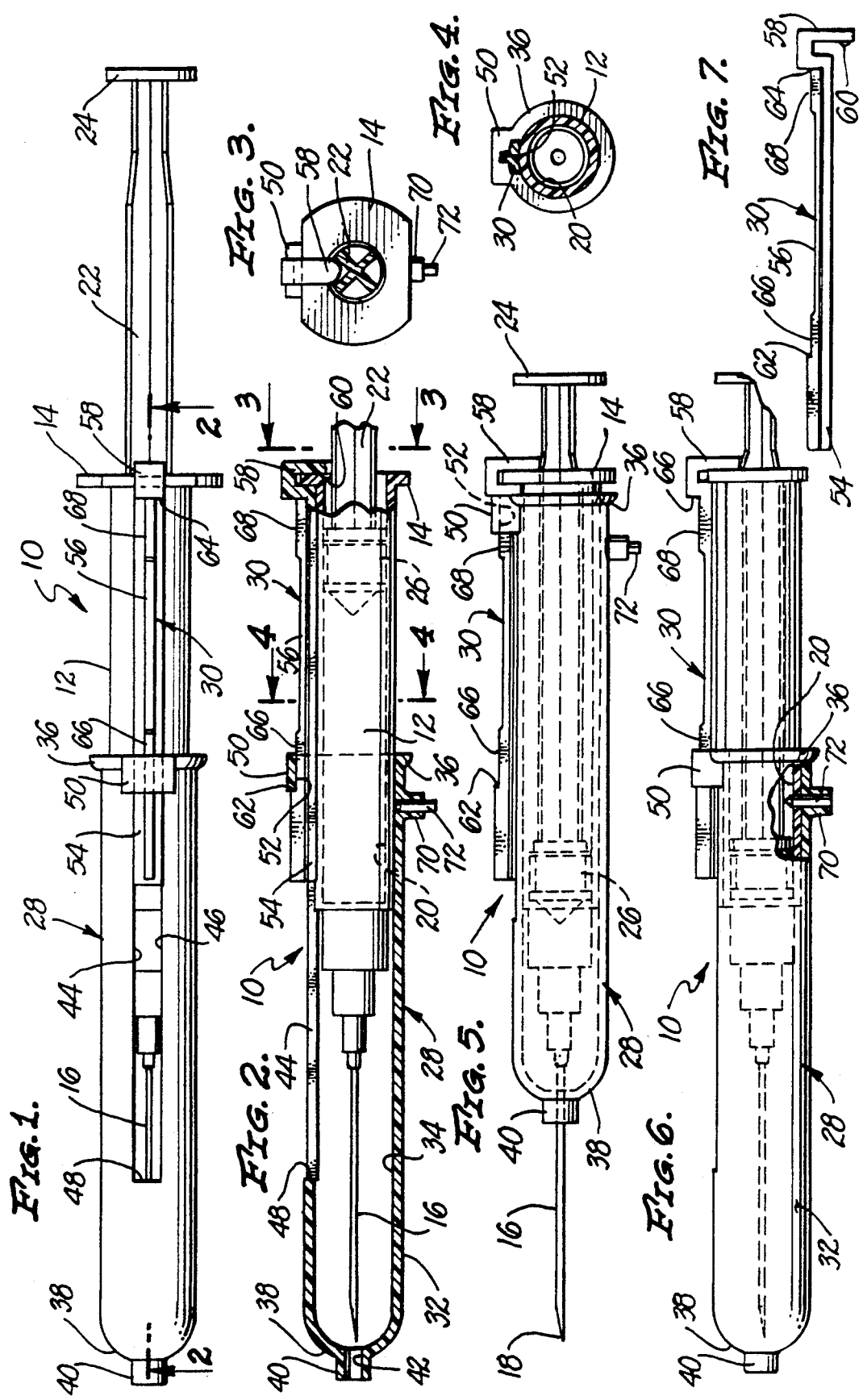

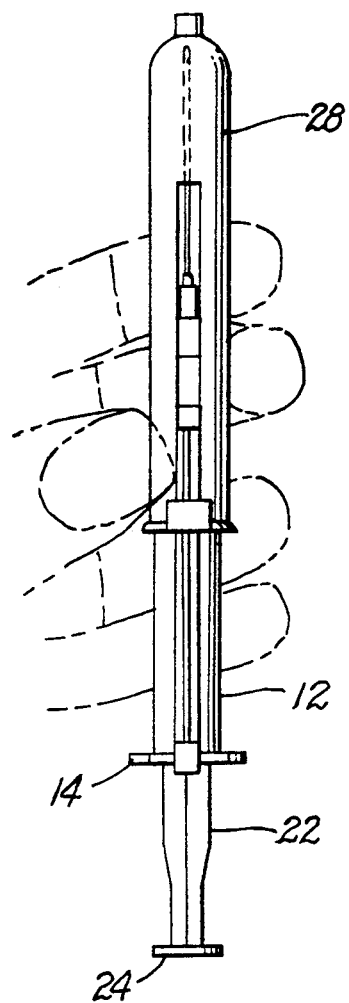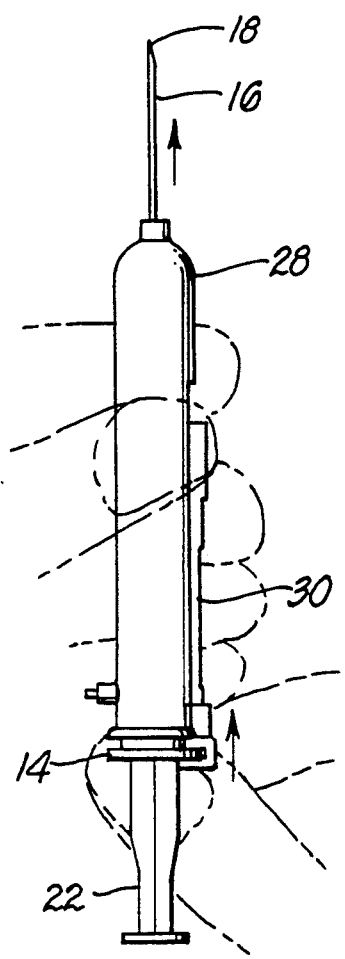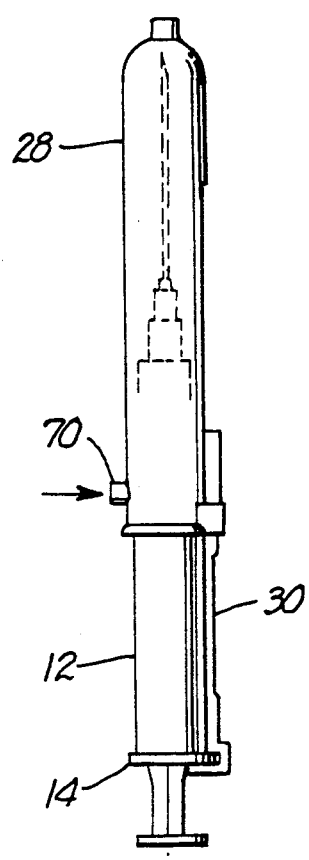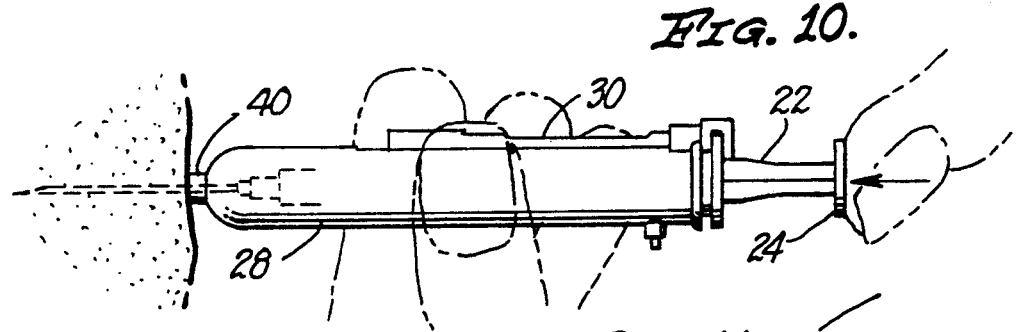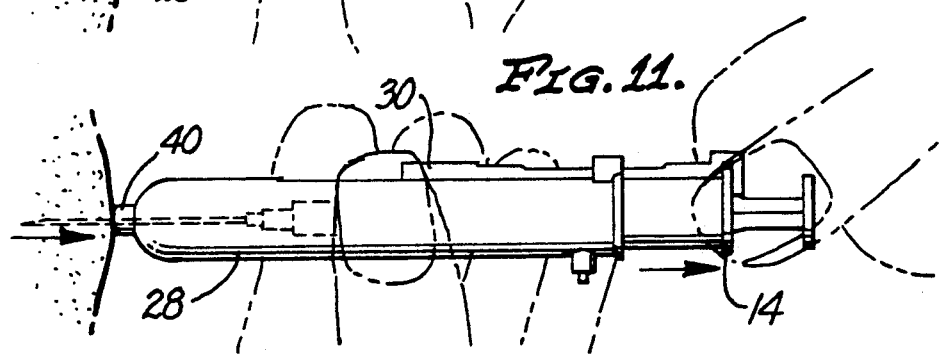

HYPODERMIC SYRINGE WITH PROTECTIVE SHIELD

FIELD OF THE INVENTION

This invention is directed to a protective shield particularly suitable for use to protect the needle on a hypodermic syringe so as to shield the needle after it has been used, to thus shield persons in the area against contamination from materials on the needle.

BACKGROUND OF THE INVENTION

Persons in the medical practice, doctors, nurses and laboratory technicians, are exposed to hypodermic needles which have been used for the injection or withdrawal of fluids from persons having various illnesses. Many diseases can be contractet this way, and the present danger of contracting Hepatitis B, Acquired Immune Deficiency Syndrome (AIDS), and other diseases causes extra caution on the part of those health professionals. A used hypodermic syringe needle is a hazard of which the health profession has become more aware since the fairly widespread distribution of these virulent strains. Thus, there is need to protect health professionals against scratching or puncture by those needles.

SUMMARY OF THE INVENTION

In order to aid in the understanding of this invention, it can be stated in essentially summary form that it is directed to a hypodermic syringe with protective shield wherein the shield slides on the barrel of a standard syringe which has a needle mounted thereon. The shield slides from a position where it completely encloses the needle to a position where it exposes the needle for use. A detent releasably holds the shield in either of its end positions. When use is completed, a locking pin is pressed from the shield into the syringe barrel to lock the needle in protected position.

It is thus a purpose and advantage of this invention to provide a hypodermic syringe with a protective shield so that the shield protects the used syringe needle to prevent accidental harm therefrom.

It is another purpose and advantage of this invention to provide a hypodermic syringe which carries a needle thereon with a protective shield, altogether for enclosure and sterilization so that a sterile, single-use syringe is provided with a protective shield.

It is another purpose and advantage of this invention to provide a protective shield which has a locking pin therein so that, once the syringe is used and the protective shield is positioned over its needle, the locking pin can be inserted to retain the shield in place and to puncture the syringe barrel.

Other purposes and advantages of this invention will become apparent from a study of the following portion of the specification, the claims and the attached drawings.

BRIEF DESCRIPTION OF THE DRAWINGS

FIG. 1 is a side-elevational view of the hypodermic syringe with protective shield in accordance with this invention with the protective shield in protective position and the syringe plunger withdrawn.

FIG. 2 is a section through the protective shield with the hypodermic syringe mostly in side elevation, as shown generally along line 2-2 of FIG. 1.

FIG. 3 is a view of the end of the syringe barrel, as seen generally along line 3-3 of FIG. 2.

FIG. 4 is a section through the syringe barrel showing the protective shield in end elevation, as seen generally along line 4-4 of FIG. 2.

FIG. 5 is a side-elevational view of the hypodermic syringe with its protective shield drawn up the syringe barrel into the non-protected position for use of the syringe.

FIG. 6 is a side-elevational view with parts broken away of the syringe after use with the shield in the extended, protective position, and showing the locking pin in place.

FIG. 7 is a side-elevational view of the detent which releasably holds the protective shield in its end positions with respect to the syringe barrel.

FIGS. 8, 9, 10, 11 and 12 show the sequence of steps of use of the hypodermic syringe with protective shield in accordance with this invention.

DESCRIPTION OF THE PREFERRED EMBODIMENT

Hypodermic syringe 10 is a standard medical type hypodermic syringe. It has a barrel 12 which carries finger flange 14 on the rear end thereof and a hypodermic needle 16 at the front end thereof. The needle has a sharp tip 18. The syringe has a bore 20 therein which is in fluid communication with the passage through the needle to the tip of the needle. Hypodermic plunger 22 is slidable within the bore. The plunger carries a thumb pad 24 on the outer end and a piston 26 on the inner end thereof. The piston is in slidable, but sealing relation with respect to the bore so that, when the thumb is used to press the plunger forward into the barrel, the contents of the barrel forward of the plunger are expelled through the needle. Such a structure is commonly used for injecting medication into a patient. It is also used for withdrawing blood and other body fluids for laboratory analysis. The problem is protecting the sharp tip 18 of the hypodermic needle after it has been used.

Protective shield 28 provides this protection, and its detent 30 aids in the control of the protective shield along the length of the barrel of the hypodermic syringe. Protective shield 28 has a generally cylindrical exterior surface 32 and a generally cylindrical interior surface 34 coaxial therewith to define a thin walled tube. The interior diameter is such as to slidably receive the barrel 12 of the syringe 10. Shield 28 is provided with a flange 36 at its near end and a hemispherical closure 38 at its far end. The closure 38 is provided with a cylindrical boss 40 which has a needle opening 42 therethrough. The hemispherical closure, boss 40 and needle opening 42 are substantially coaxial with the surfaces of the protective shield. The needle opening is in alignment with needle 16. The length of the shield is such that, when it is in its forward position, shown in FIGS. 1, 2, 6, 8 and 12, the needle is fully enclosed by protective shield 28.

The position of the shield on the syringe barrel is controlled by detent 30. As is seen in FIGS. 1, 2, 5, 6 and 7, detent 30 is an elongated structure. The protective shield has a slot therein defined by longitudinal walls 44 and 46. The slot extends from the flange end of the body of the protective shield about two-thirds the way down to terminate in a front wall 48. The sides of the protective shield on the opposite sides of the slot are joined at the flange end by bridge 50. The underside of the bridge has a groove 52 therein, see FIG. 2, to accommodate a portion of the detent. The detent 30 is elongated, and its body 54 is an axially cut section of a cylindrical tube sized to lie within the longitudinal slot in the protective shield. Its interior and exterior surfaces are in alignment wi&h the interior and exterior surfaces 34 and 32 of the protective shield. Stop rail 56 is axially positioned on top of body 54, centrally between the sides thereof. Stop rail 56 fits within groove 52 in bridge 50.

Detent 30 is engaged on the syringe barrel so that it is always axially located with respect to the syringe barrel. This is accomplished by means of hook 58, which is formed as part of the detent and engages over the finger flange 14 on the syringe barrel. The hook engages all the way to the inside of the syringe barrel where a knob 60 resiliently engages within the syringe barrel to hold the detent in place. The plunger 22 is cross-shaped, as seen in FIG. 3, and the hook is accepted between the flanges of the cross, as seen in FIG. 3.

The detent is, thus, axially located with respect to the syringe barrel and serves to control the positioning of the protective shield 28 with respect to the syringe barrel. Positive stops are provided for this motion by stop shoulders 62 and 64. In FIG. 5, the bridge 50 is shown as engaged against the stop shoulder 64 to define the rearward limit of the protective shield, which is the position in which the needle is exposed. The forward limit position is shown in FIGS. 1, 2 and 6 where the bridge 50 is engaged against the stop shoulder 62. In this position, the needle 16 is totally enclosed within the protective shield 28. In this way, the detent 30 limits the end motions of the protective shield. However, in addition, the stop rail 56 of the detent 30 has detent shoulders 66 and 68. When the bridge 50 approaches one of the shoulders 66 or 68, the dimensions are such that the bridge may rise up thereover, but the free sliding of the protective shield is inhibited. The detent shoulder jams under the bridge so that changing the position of the protective shield 28 on the syringe barrel can only be accomplished with strong force. In fact, the detent shoulder 66 is sufficiently strong so that, if the assembly of FIGS. 1 and 2 is dropped needle-down, the impact force is insufficient to drive the bridge off of the detent shoulder 66 so that the needle 16 remains sheathed. That is the purpose of detent shoulder 66. The purpose of detent shoulder 68 is to inhibit inadvertent sliding of the protective shield 28 when the needle is in the use position of FIG. 5. The manner in which the stop rail 56 engages under bridge 50 is seen in FIG. 4.

Upon completion of the single use, it is desirable to dispose of the syringe so that it cannot be reused. Boss 70 is formed on the side of the shield 28 near its flange 36. The boss is positioned so that, when the protective shield 28 is in its forward position and the plunger 22 is in its forward position, the flange lies behind piston 26 on the plunger. Boss 70 has a hole therethrough and has a destruction pin 72 in press-fit therein. In normal position, as shown in FIG. 2, the destruction pin does not reach beyond the interior surface 34 of shield 28, so that it is outside of the syringe barrel. Destruction pin 72 extends out of the boss in that position, as shown in FIG. 2. The destruction pin is sufficiently sharp and is sufficiently long so that, when the procedure with the hypodermic syringe with its protective shield is completed, the destruction pin is thrust inward to penetrate the barrel of the syringe and extend behind the piston 26 to prevent its withdrawal. The inserted position of the destruction pin is shown in FIG. 6.

FIGS. 8 through 12 show the manner of use of the hypodermic syringe with its protective shield to perform a procedure including complete protection of the user from the used needle. The syringe with its shield is initially positioned, as is shown in FIG. 8, and is usually provided within a sterile package. The sterile packaging is removed, and the shield is held in the left hand of the medical professional. The right thumb and forefinger grasp the finger flange, and the left hand draws the protective shield 28 toward the user. Forward is the distal position away from the user, and back is the proximal position toward the user. It is appreciated that it is relative motion of the protective shield on the syringe barrel, but in this description, it is assumed that the syringe barrel is stationary and the shield is moving forward and back thereon. The shield is brought to the rearmost position, as shown in FIG. 9. Needle 16 is exposed, and the syringe is usually filled with medication by placing the needle in a liquid medication vessel and withdrawing the plunger 22. The syringe is ready for normal use with the shield drawn back up on its rear detent shoulder 68 against its rear stop 64. Thereupon, the needle 16 is inserted into the patient, as is shown in FIG. 10. With the left hand grasping the shield, which is locked to the syringe barrel, plunger 22 is thrust in by pressing the right thumb on thumb pad 24 to inject the medication into the patient.

When injection is completed, the left hand of the medical professional, still grasping the protective shield 28, as seen in FIG. 11, holds its boss 40 against the patient, as is seen in FIG. 11. While the left hand holds the protective shield 28 in place, grasp by the right forefinger and thumb on finger flange 14 of the syringe permits withdrawal of the syringe and needle backward with respect to the protective shield, as shown in FIG. 11. The needle 16 is completely enclosed as it is withdrawn from the patient. When the syringe barrel is pulled completely back so that the stop shoulder 62 engages against bridge 50, the detent shoulder 66 is sufficiently strong to prevent inadvertent forward motion of the needle with respect to the protective shield, even if the assembly is dropped on boss 40. During the entire withdrawal of the needle from the patient end, the needle has been protected; when the needle is fully withdrawn into the protective shield, the needle remains fully protected. In this position of the protective shield and syringe, the destruction pin 72 is pressed in by application of force in the direction of the arrow in FIG. 12. The pin is engaged against the hard surface, and a moderate thrust will move the destruction pin into syringe barrel-locking position. This is double protection that the needle cannot be exposed. The entire assembly can be disposed of without danger of contamination of those around it by the contents of the syringe.

This invention has been described in its presently contemplated best mode, and it is clear that it is susceptible to numerous modifications, modes and embodiments within the ability of those skilled in the art and without the exercise of the inventive faculty. Accordingly, the scope of this invention is defined by the scope of the following claims.

What is claimed is;

1. A protective shield of a hypodermic syringe having a barrel with the barrel having a needle end and a plunger end, with a needle on the needle end of the barrel and a plunger extending into the barrel from the plunger end;

a tubular body positioned on the barrel of the syringe and sized to slidably engage upon the barrel of the syringe and to slide from a forward position to a rearward position on the syringe barrel, said protective shield having an opening in its forward end so that the needle on the hypodermic syringe is exposed through said opening when said protective shield is in its rearward position on the syringe barrel and said protective shield is sufficiently long so that when in its forward position the needle on the hypodermic syringe is enclosed within said protective shield;

means interconnecting the barrel of the syringe with said protective shield to limit motion of said protective shield with respect to the barrel to motion between the forward position and rearward position; and a destruction pin mounted in said shield for motion with respect to said shield in a direction at an angle with respect to the motion of said shield on said barrel, said destruction pin having a first position where it extends from said shield and permits motion of said shield with respect to the barrel and a second position wherein said destruction pin is thrust through the syringe barrel, said destruction pin being positioned so that when said shield is in its forward position covering the needle, said destruction pin can be thrust through the syringe barrel to lock said protective shield in needle-covering position.

2. The protective shield of claim 1 wherein said protective shield has a closure on the forward end thereof and said closure has said needle opening therethrough.

3. The protective shield of claim 2 wherein said closure includes a boss and said boss has said needle opening therethrough.

4. The protective shield of claim 1 wherein said means interconnecting said shield and the barrel of the hypodermic syringe is an elongated detent.

5. The protective shield of claim 4 wherein said detent has a hook thereon for engagement with the barrel of the syringe and has first and second stop shoulders thereon, said protective shield having engagement means thereon for selective engagement with said first and second stop shoulders to limit the motion of said protective shield with respect of the syringe barrel to define the forward and rearward positions of said protective shield.

6. The protective shield of claim 5 wherein said engagement means comprises a bridge on said shield engaging over said detent so that said bridge selectively engages said first and second stop shoulders to limit motion of said shield.

7. The protective shield of claim 6 further including first and second detent shoulders adjacent said first and second stop shoulders so that when said bridge approaches said first stop shoulder it first engages said first detent shoulder to releasably hold said protective shield in its forward position.

8. The protective shield of claim 5 further including first and second detent shoulders, said stop shoulder engagement means also including detent shoulder engagement means so that said first detent shoulder releasably retains said protective shield in its forward position when said first stop shoulder is engaged by said engagement means.

9. The protective shield of claim 8 wherein said protective shield has a closure on the forward end thereof and said closure has said needle opening therethrough.

10. The protective shield of claim 9 wherein said closure includes a boss and said boss has said needle opening therethrough.

11. The protective shield of claim 1 wherein the plunger has a plunger piston thereon, said destruction pin being positioned so that when said shield is in its forward position covering the needle and the plunger is thrust into the barrel, said destruction pin can be thrust through the syringe barrel behind the plunger piston to lock said protective shield in needle-covering position and lock the plunger in the barrel.

12. A hypodermic syringe with a protective shield thereon, comprising:

a syringe having a barrel having an axis and having an external surface generally parallel to said axis, said syringe having a needle on one end thereof extending generally parallel to said axis;

said protective shield having walls slidably engaging on said syringe, said shield being slidable on said syringe barrel from a protective position wherein said needle is surrounded by said walls of said protective shield to a retracted position wherein said needle is exposed beyond said protective shield;

means interengaging said protective shield and said syringe barrel so as to limit motion of said protective shield on said syringe barrel from said extended position to said retracted position; and a destruction pin slidably mounted in said wall of said protective shield and positioned so that when said protective shield is in its needle-protecting position, said destruction pin can be pressed from a first position where it extends out of said wall of said protective shield to a second position where it extends through said syringe barrel to lock said protective shield in protective position.

13. The hypodermic syringe with protective shield of claim 12 wherein said means comprises a detent having a hook thereon engaged on said barrel and having stop shoulders thereon, said protective shield having a stop thereon for engagement with said stop shoulder sin said limit positions of said protective shield on said syringe barrel.

14. The hypodermic syringe with protective shield of claim 13 wherein said protective shield has guide walls therein and said detent lies within said guide walls and said stop is a bridge across said detent over said side walls.

15. The hypodermic syringe with protective shield of claim 13 further including detent shoulders adjacent said stop shoulders so that when said protective shield is positioned with said stop against one of said stop shoulders, one of said detent shoulders releasably retains said protective shield in position.

16. The hypodermic syringe with protective shield of claim 15 wherein said protective shield has guide walls therein and said detent is guided with respect to said guide walls and said stop is a bridge over said detent and across said guide walls.

17. The hypodermic syringe with protective shield of claim 12 further including a plunger in said syringe barrel, said plunger having a piston thereon, said destruction pin being positioned so that when said protective shield is in its needle-protecting position and said plunger is thrust into said syringe barrel, said destruction pin can be pressed through the syringe barrel behind said plunger piston to lock said protective shield in protective position and lock said plunger in said syringe barrel.

18. The process of protecting against needle contamination with a syringe having a protective shield which slides on the barrel of the syringe from an extended, protective position to a retracted, needle-exposed position, comprising the steps of:

graphing the protective shield in the retracted position on a syringe filled with medication;

inserting the needle into the patient and actuating the plunger of the syringe for fluid transfer between the patient and the syringe;

grasping the protective shield in one hand and holding it against the patient's epidermis while the needle is within the patient;

withdrawing the syringe barrel from the protective shield and drawing the needle into the protective shield while the protective shield remains against the patient's epidermis, surrounding the needle so that the needle is withdrawn from the patient into the protection of the protective sheath without the needle being exposed to its surroundings; and thrusting a destruction pin through the protective sheath and through the syringe barrel while the protective sheath is in the extended position to lock the protective sheath in the extended position while it surrounds the needle.

19. The process of claim 18 further including the preliminary steps of removing the hypodermic syringe and its protective shield from a sterile environment while the protective shield is extended to enclose the hypodermic needle; and thereafter, while drawing the protective sheath back on the syringe barrel to expose the needle so as to draw medication into the syringe barrel through the needle.

* * * * *